United States Patent [19]

Selhub et al.

[11] 4,273,757
[45] * Jun. 16, 1981

[54] DETERMINATION OF TRANSCOBALAMINS

[75] Inventors: Jacob Selhub, Chicago, Ill.; Bracha Rachmilewitz; Nathan Grossowicz, both of Jerusalem, Israel

[73] Assignee: Yissum Research Development Company, Jerusalem, Israel

[*] Notice: The portion of the term of this patent subsequent to Sep. 11, 1996, has been disclaimed.

[21] Appl. No.: 961,771

[22] Filed: Nov. 17, 1978

Related U.S. Application Data

[63] Continuation-in-part of Ser. No. 802,379, Jun. 2, 1977, Pat. No. 4,167,556.

[51] Int. Cl.³ .................. G01N 33/48; A61K 43/00
[52] U.S. Cl. .................................. 424/1; 424/12; 23/230 B
[58] Field of Search .................. 424/172; 23/230 B

[56] References Cited

U.S. PATENT DOCUMENTS

| | | | |
|---|---|---|---|
| 3,937,799 | 2/1976 | Lewin et al. | 424/1.5 |
| 4,146,602 | 3/1979 | Gutcho et al. | 424/1 |
| 4,167,556 | 9/1979 | Selaub et al. | 424/1 |

Primary Examiner—Benjamin R. Padgett
Assistant Examiner—Christine M. Nucker
Attorney, Agent, or Firm—Andrew L. Klawitter

[57] ABSTRACT

A process and test kit for the quantitative determination of the individual and total unsaturated Vitamin B-12 binding capacities of the three transcobalamins TC-I, TC-II, and TC-III in serum. The process comprises incubating a serum sample with a solution of $^{57}$Co Vitamin B-12, contacting the resulting mixture with a TC-II adsorbent and with a DEAE-cellulose adsorbent for TC-I and TC-III, measuring the total radioactivity adsorbed to said adsorbents, selectively desorbing TC-III from the DEAE-cellulose adsorbent by washing with a monopotassium phosphate solution of about 0.05 M and at a pH of about 4.6, measuring the individual radioactivity adsorbed to each of said adsorbents, and calculating the radioactivity that had been washed from the DEAE-cellulose adsorbent by said phosphate solution. The resulting four radioactivity values are functions of the total, TC-II, TC-I, and TC-III unsaturated Vitamin B-12 binding capacities, respectively, of the serum tested. The test kit comprises the essential elements for performing the present process.

22 Claims, No Drawings

DETERMINATION OF TRANSCOBALAMINS

CROSS-REFERENCE TO RELATED APPLICATION

This application is a continuation-in-part of U.S. Ser. No. 802,379, filed June 2, 1977, now U.S. Pat. No. 4,167,556.

BACKGROUND OF THE INVENTION

1. Field of the Invention

The human serum contains at least three known binders of Vitamin B-12, namely the three transcobalamins designated as TC-I, TC-II, and TC-III. TC-I and TC-III are derived from granulocytes and both are alpha-globulins with a similar molecular weight, of about 120,000. They have a different electrical charge and hence differ in their electrophoretic mobility. TC-II is a beta-globulin of molecular weight of about 38,000 and it is derived mainly from the liver. The physiological functions of the three transcobalamins are not fully understood, but it is known that endogenous Vitamin B-12 is bound mainly to TC-I (about 85%), and TC-II binds about 15% of endogenous B-12 while TC-III seems to bind Vitamin B-12 only in vitro. Since TC-II binds small quantities of endogenous B-12 while it takes up the main part of Vitamin B-12 added to the serum in vitro, most of the unsaturated B-12 binding sites are located on TC-II (unsaturated B-12 binding capacity, UBBC). Vitamin B-12 is bound in the serum to the transcobalamins in a 1:1 molar ratio.

It is well known that certain pathological conditions are associated with significant specific changes in the level of the three transcobalamins in serum and that the determination of the Vitamin B-12 binding capacity of each of the three transcobalamins is an important tool in medical diagnosis. Amongst others, the quantitative determination of the B-12 binding capacity of the three transcobalamins is of value in the effective screening of certain malignant diseases and also in the monitoring of the treatment of these diseases. Amongst others, the determination of the three transcobalamins is of value in:

A. Diagnosis, evaluation of treatment and monitoring of the course of myeloproliferative diseases [CML (chronic myelocytic leukemia), APL (acute promyeolocytic leukemia), polycythemia vera.]
B. Differentiation of leukemoid reactions and conditions manifested by non-leukemic leukocytosis.
C. Recognition of rapid malignant cell proliferation in lymphoma, sarcoma, Hodgkins Disease, actue leukemia, etc.
D. Evaluation of therapy and monitoring the course of malignant diseases (remission and relapse) such as sarcomas, actue leukemias, Hodgkins Disease, lymphomas etc.
E. Diagnosis and recognition of hepato-cellular damage.

The quantitative determination of B-12 binding capacity of the three transcobalamins may also be of value in the recognition, differentiation and monitoring of various other disorders.

2. Brief Description of the Prior Art

The three transcobalamins present in human serum are difficult to separate and their quantitative determination is both complicated and time-consuming. The main problem is the similarity of electrophoretic properties of TC-II and TC-III and their similar behavior on DEAE-cellulose separation.

The prior art techniques for separating the transcobalamins are characterized by the methods described in the following references: *Blood* 33:899(1969), *Br. J. Haematol.* 22:33 and 53(1972), *J. Lab. Clin. Med.* 73:60(1969), *Am. J. Clin. Pathol.* 62:367(1974), *Blood* 31:518(1968), *Blood* 25:875(1965), *Fed. Proc.* 33:715(1974), *blood* 45:281 and 287(1975), *J. Lab. Clin. Med.* 75:673(1970), *Proc. Soc. Exp. Biol. Med.* 147:377 (1974), and *J. Biol. Chem.* 250:7700(1975). These prior art techniques are cumbersome research techniques and some are even known to give inconsistent results. Some require days to complete and all have to be considered as confined to use in the research laboratory.

An object of the present invention is to provide a process and test kit for transcobalamin determination which is applicable to routine use in the clinical laboratory. The present inventors, in *FEBS Letters* 44:71(1974), described an advantageous technique for the separate determination of TC-I and TC-II, but made no suggestion as to the determination of TC-III as well, which substance has properties similar to TC-I.

SUMMARY OF THE INVENTION

The present invention relates to a simple and rapid process for the fractionation of the three transcobalamins from each other and for their quantitative determination. It further relates to a test kit for carrying out such fractionation and determination.

The present process enables the quantitative determination of the individual TC-I, TC-II and TC-III and total (UBBC) unsaturated Vitamin B-12 binding capacities in a predetermined quantity of serum. In the process, the serum sample is incubated with radioactive $^{57}$Co Vitamin B-12 so that the unsaturated Vitamin B-12 binding sites on the transcobalamins from the serum sample become occupied with radioactive Vitamin B-12. Separation of the excess $^{57}$Co Vitamin B-12 and measurement of the radioactivity that has become bound to TC-I, TC-II, or TC-III, measured as a total amount or as individual amounts, will yield values which are a function of the unsaturated binding capacities in the serum. This is accomplished by contacting the mixture with (a) a TC-II adsorbent, such as a cellulose nitrate filter or granular silica gel, whereby the TC-II from the serum sample becomes adsorbed thereto, and (b) a DEAE-cellulose adsorbent whereby the remaining transcobalamins, TC-I and TC-III, become adsorbed thereto. The excess radioactive Vitamin B-12 is then readily washed away from the adsorbents with an appropriate liquid, usually a buffer solution. The total radioactivity of the washed adsorbents combined can then be measured and is a function of the total unsaturated Vitamin B-12 binding capacity of the serum tested. The radioactivity of the TC-II adsorbent can be separately measured and, of course, is a function of the TC-II unsaturated Vitamin B-12 binding capacity of the serum tested.

Separate determination of the TC-I and TC-III unsaturated Vitamin B-12 binding capacities requires the selective desorption of one thereof from the DEAE-cellulose adsorbent. This step is uniquely performed according to the present invention by washing the adsorbent with a monopotassium phosphate solution of about 0.05 M and at a pH of about 4.6 which selectively desorbs TC-III. The radioactivity of the washed DEAE-cellulose adsorbent can then be measured and is a function of the TC-I unsaturated Vitamin B-12 binding capacity of the serum tested. By calculating the difference in radioactivity between the total radioactivity measurement (related to UBBC) and the sum of the individual radioactivity measurement related to TC-II and TC-I binding capacities, the TC-III unsaturated Vitamin B-12 binding capacity is determined. As demonstrated in the examples below, the radioactivity values for the UBBC and the TC-I, TC-II and TC-III binding capacities can be converted to Vitamin B-12 concentration values by comparison of the UBBC, or total radioactivity value to the radioactivity of a solution of $^{57}Co$ Vitamin B-12 of known concentration and calculating the fractions thereof attributable to TC-I, TC-II, and TC-III.

The TC-II adsorbent may be made of any material known for this purpose and preferably is of a charged cellulose material, such as a cellulose nitrate filter, or a granulated silica gel such as the material commonly known as QUSO. The DEAE-cellulose adsorbent likewise may be in the form of filter or in a granular form. When such adsorbents are in the form of filters, a useful separation device takes the form of a stack of one or more of each of such filters held in a column arrangement. On the other hand, when such adsorbents are in their granular forms, a useful separation device takes the form of separate small columns, or mini-columns as they are often referred to, which are stackable for purposes of flowing liquid from one column to the other. Specific examples of such filter stack device and such mini-column devices are described below, however, it will be recognized that there are a variety of evident modifications thereof and of the general use of a TC-II adsorbent and a DEAE-adsorbent which will not depart from the inventive scope hereof.

The entire procedure, whether using the filter stack or mini-column arrangement, is carried out in a rapid and continuous sequence of steps which can be completed within one hour and a plurality of samples can be tested simultaneously. The adsorptions and desorption are both specific and quantitative and thus provide a test of high accuracy and entirely adequate for clinical purposes.

FILTER STACK EXAMPLE

I. Materials

1. Cellulose nitrate filter discs, 25 mm in diameter (Schleicher and Schull, Dassel, Germany).
2. DEAE-Cellulose (DE-81) filter discs, 25 mm in diameter (The Whatman Biochemicals Ltd., Maidstone, Kent, England).
3. Millipore type filter holder apparatus for 25 mm discs, (The Tamar Co., Jerusalem, Israel).
4. $^{57}Co$ B-12, high specific activity (135–200 $\mu Ci/\mu g$, the Radiochemical Centre, Amersham, Bucks, England). Batches of 10 $\mu Ci$ were diluted with water to a final concentration of 10,000 pg B-12/ml and stored in the refrigerator until ready for use.
5. Borate buffer, 0.1 M Sodium Borate adjusted to pH 8.5 with 10 M NaOH, prepared in glass distilled water and filtered through cellulose-nitrate filter to remove particles that may interfere with the assay.
6. Phosphate solution, 0.05 M monopotassium phosphate (pH 4.6) prepared in glass distilled water, and filtered through cellulose-nitrate filter as described above. The concentration of the phosphate is quite critical. No satisfactory separation can be obtained at lower or at higher concentrations.

II Procedure (A) Determination of UBBC

The filter discs were arranged in a stack with one cellulose-nitrate disc which was previously immersed in distilled water, on top of three DE-81 discs. The stack was placed in the millipore filter holder and washed with glass distilled water before use. Duplicate samples of the serum (0.01 ml each) were incubated for 30 min at 37° (with excess of $^{57}Co$ B-12 (100 pg/0.01 ml) and 0.2 ml 0.1 M Sodium Borate buffer (pH 8.5). After incubation, the mixture was diluted to 1–12 ml with the borate buffer and passed by applying vacuum through the filter stack. The excess unbound $^{57}Co$ B-12 was removed by washing the filter twice, with 10 ml of the same borate buffer. The unsaturated B-12 binding capacity (UBBC, expressed in pg of $^{57}Co$ B-12 bound per ml of serum) was calculated from the radioactivity retained by the stack.

(B) Determination of TC-I, II and III binding capacity

The duplication samples of serum treated as described for the determination of UBBC and passed through the filter stack by applying vacuum. The excess unbound $^{57}Co$ B-12 was removed as descrribed above. Under these conditions TC-II is selectively and quantitatively adsorbed onto the cellulose-nitrate filter, while both TC-I and TC-III are adsorbed onto the DE-81 filters. After the filter stack was washed to remove the excess of $^{57}Co$ B-12, the cellulose-nitrate filter was removed and counted (the first count). This count represents the unsaturated binding capacity of TC-II. The DE-81 filter stack was washed with 5 ml borate buffer and counted (the second count). This count represents the unsaturated binding capacity of TC-I and TC-III remaining on the DE-81 filter discs. Transcobalamins I and III were separated by washing the De-81 filter stack with 15 ml of 0.05 M monopotassium phosphate solution (pH 4.6). The stack was again counted (the third count). This count represents the unsaturated binding capacity of TC-I adsorbed on the stack after TC-III was removed by the monopotassium phosphate solution. The unsaturated binding capacity of TC-III is given by the difference between the second and third counts.

The results obtained by the above procedure were checked with a number of the established laboratory procedures known in the art and a good agreement was obtained. The entire procedure according to the present invention can be carried out in about one hour and many samples can be tested simultaneously. Thus this novel method provides an important novel clinical test which is of great diagnostic value and which permits one to obtain results in an easy, speedy and efficient manner.

It ought to be stressed that various attempts have been made to separate transcobalamins by DEAE cellulose-chromatography. Various authors have reported experiments at pH 5.8 with 0.1 M sodium phosphate; at pH 6.35 with 0.06 M phosphate buffer; at pH 6.2 with 0.975 M phosphate buffer; at pH 6.3 with gradient of phosphate buffer 0.06 M and 1 M NaCl; a gradient of 0.01 M phosphate buffer (pH 8.0) and 0.3 M (pH 4.5). None of the above separation procedures was useful for an acceptable quantitative separation of the two transcobalamins I and III. The results obtained with sodium phosphate buffers, with monosodium phosphate and with potassium phosphate buffers were inconsistent and did not give the required separations. The concentration of 0.05 M monopotassium phosphate is quite critical. It may vary from about 0.045 to about 0.55, but at lower or higher concentrations inferior separations of TC-III from TC-I are obtained. The high pH of the borate buffer is a requisite for the selective adsorption of the TC-II on the cellulose nitrate filter.

Instead of the DEAE-cellulose filters there may be used DEAE-Sephadex mini-column. The filter media used according to the above description can of course be used in column form.

The present invention also relates to test means in kit form, comprising the necessary selective separation means, such as filter-column or stack, chemicals for the required solutions and $^{57}$Co Vitamin B-12 solution.

MINI-COLUMN EXAMPLE

Separation of the three transcobalamins (I, II, III) can also be achieved by a two step filtration using a double mini-column device. After separation, the Unsaturated (B-12) Binding Capacity of each transcobalamin is determined by measuring each fraction for remaining radioactivity (i.e., the amount of $^{57}$Co-B-12 bound from the starting reaction mixture) and comparison to a calibrated solution of radioactive $^{57}$Co-B-12 (containing a known amount of Vitamin B-12 in pg/ml).

The double column device consists of:

(1) an upper column containing 30 mg cellulose DE-23 Whatman in phosphate buffer (pH 6.4, 0.02 M) held between two vyon discs and equiped with a bottom cap.

(2) a lower column containing 100 mg silica gel (QUSO) in borate buffer (1 M, pH 7.9), held between two vyon discs and equiped with a bottom cap.

The upper column is connected to the lower column by a small plastic adaptor which serves as the liquid transport device between the two columns, as well as an air depressurizer. Another extra plastic part useful in the double column operation is a 25 ml plastic funnel that can be connected to the upper column, serving as a buffer reservoir container.

The assay procedure is as follows:

(1) Place 50 μl of $^{57}$Co-B-12 solution on top of disc of the upper DE-23 column (bottom cap is closed). ($^{57}$Co-B-12 solution having a defined specific activity and concentration of Vitamin B-12 to yield 2000 pg/ml).

(2) Add 10 μl of the serum sample, mix well, let incubate for 10 minutes.

(3) Open bottom cap of this column and fix it on the silica column, through the column adaptor.

(4) Connect the plastic funnel and wash with 25 ml of phosphate buffer (pH 6.4 0.02 M).

(5) After all the solution has drained off the two columns, disconnect them and measure the $^{57}$Co radioactivity of:
 (a) cellulose DE-23 upper column=c.p.m. No. 1
 (b) silica bottom column=c.p.m. No. 2
 This counting step can be done in any Gamma counting instrument equipped with $^{57}$Co isotope channel.

(6) The DE-23 upper column is washed a second time with 25 ml of monopotassium phosphate solution (pH 4.6, 0.05 M using again the plastic funnel.

(7) Count this column again after washing is completed:

(c) second count of the upper column=c.p.m. No. 3

(8) Count simultaneously a sealed tube containing calibrated solution of $^{57}$Co-B-12 containing 100 pg Vitamin B-12 per ml.

(9) calculations:

$$\frac{c.p.m. 1 + c.p.m. 2 \times 10^4}{c.p.m. \text{ of calibrator}} = \text{UBBC in pg Vit B-12 ml} \quad (a)$$
(total serum Unsaturated B-12 Binding Capacity)

$$\frac{c.p.m. 3 \times \text{UBBC pg Vit. B-12/ml}}{c.p.m. 1 + c.p.m. 2} = \text{TC-I in pg Vit. B-12/ml sera} \quad (b)$$

$$\frac{c.p.m. 2 \times \text{UBBC pg Vit. B-12/ml}}{c.p.m. 1 + c.p.m. 2} = \text{TC-II in pg Vit. B-12/ml sera} \quad (c)$$

(d) UBBC−(TC−I+TC−II)=TC−III in pg Vit. B-12/ml sera.

This mini-column procedure can be used for the same purposes as described above for the filter stack procedure.

Results obtained using the filter stack and double mini-column formats indicate that various pathological changes can be readily differentiated by means of the results obtained by the above method of determination of TC-I, TC-II, and TC-III.

Extensive experiments were carried out with patients having various types of disease. The procedure used was as set out above. The results of the determinations are given in the following. The following summary of the results is grouped as follows:

Group 1: Deals with normals.
Group 2: Deals with chronic myeloid leukemia (CML) and promyelocytic leukemia (APL).
Group 3: Deals with Polyceythemia vera (PV) and leukocytosis.
Group 4: Deals with acute leukemia, Hodgkins disease and lymphoma.
Group 5: Deals with hepatocellular damage.

(a) Group 1: Normals

TABLE A(1)

| | | Filter Stack Test Format | | | |
|---|---|---|---|---|---|
| No. | Patient Identification | $B^{12}$ pg/ml | UBBC pg/ml | TCI pg/ml | TCII pg/ml | TCIII pg/ml |
| 1 | E.G. | 700 | 1884 | 301 | 1260 | 283 |
| 2 | Y. | 570 | 1764 | 317 | 1112 | 335 |
| 3 | Y.A. | 650 | 2230 | 356 | 1696 | 178 |
| 4 | A.Z. | 870 | 1605 | 224 | 1012 | 369 |
| 5 | R.M. | 950 | 2058 | 205 | 1462 | 391 |
| 6 | R.Z. | 550 | 1925 | 212 | 1501 | 212 |
| 7 | S.B | 800 | 1720 | 190 | 1204 | 326 |
| 8 | A.A | 500 | 1360 | 136 | 984 | 240 |
| 9 | Z.Y | 900 | 1760 | 229 | 1355 | 176 |
| 10 | O.Y | 540 | 1560 | 203 | 843 | 514 |
| 11 | H.D | 700 | 1400 | 196 | 868 | 336 |
| 12 | P.M | 750 | 1500 | 120 | 1185 | 195 |
| 13 | A.H | 700 | 1484 | 268 | 905 | 311 |
| 14 | S.A | 660 | 1545 | 171 | 1019 | 355 |
| 15 | B.A. | 700 | 1760 | 246 | 1144 | 370 |
| 16 | R.A.H | 700 | 1500 | 165 | 945 | 611 |
| 17 | P.G | 800 | 1588 | 159 | 1032 | 397 |

From Table A(1), one can define the ranges of transcobalamins in normal cases to be as follows:

| | | |
|---|---|---|
| TC-I | 100–350 | pg/ml |
| TC-II | 800–1700 | pg/ml |
| TC-III | 175–600 | pg/ml |

When the double mini-column test format was used with normal ranges of TC-I, II, and III were found to be those given in Table A(2).

TABLE A(2)

| | Mini-Column Test Format | |
|---|---|---|
| | Concentrations in pg/ml | |
| | Normal | Borderline | Pathologic |
| TC-I | 200–450 | 450–600 | above 600 or below 200 |
| TC-II | 800–1500 | 1500–1600 | above 1600 or below 800 |
| TC-III | 200–400 | 400–600 | above 600 or below 200 |

(b) Group 2: CML and APL

TABLE B(1)

| | | Filter Stack Test Format | | | | |
|---|---|---|---|---|---|---|
| Patient Identi- No. fication | $B^{12}$ pg/ml | UBBC pg/ml | TCI pg/ml | TCII pg/ml | TCIII pg/ml | Remarks |
| 1 R.M | 1500 | 6098 | 3780 | 1255 | 1063 | |
| 2 A.R | 3000 | 6823 | 4571 | 1500 | 752 | |
| 3 S.A | 2300 | 6352 | 3898 | 1674 | 780 | |
| 4 C.P | 4000 | 3623 | 2174 | 1196 | 253 | |
| 5 Z.S | 1300 | 3085 | 740 | 1666 | 679 | in remission |
| 6 A.Y | 800 | 2235 | 290 | 1230 | 715 | in remission |
| 7 P.H | 1000 | 2117 | 509 | 1025 | 583 | in remission |
| 8 A.I | 1600 | 3970 | 1192 | 1627 | 1151 | |
| 9 Y.M | 1140 | 3394 | 1086 | 1459 | 849 | |
| 10 C.Z | 4000 | 2945 | 1537 | 1030 | 878 | |
| 11 Z.B | 1400 | 2747 | 1100 | 1330 | 317 | |
| 12 B.A | 2750 | 6461 | 3941 | 1163 | 1358 | |
| 13 D.T | 3000 | 6740 | 3628 | 1550 | 1562 | |
| 14 R.A | 3200 | 3660 | 1756 | 1574 | 330 | |

In CML and APL cases there is elevation in UBBC, due to increase in TCI binding capacity, resulting in high serum $B^{12}$ levels.

The increase in TCIII binding capacity is an expression of the chronicity of the disease, because of the more mature cells present in the population which produce mainly TCIII. The TCI binding capacity decreases during chemotherapy and this serves as a reliable criterion in the evaluation of the effect of the therapy. Patients in remission, show normal to slightly elevated ranges of TCI (patients Nos. 5–7). Thus, the test for TCI contributes to monitoring the course of chronic myeloid leukemia (remission, relapse and acute crisis) and the response to chemotherapy.

Using the double mini-column test format, a precision study was performed with clinical sera from pathological conditions. Representative results are given in Table B(2).

TABLE B(2)

| | Mini-Column Test Format | | | | | | | |
|---|---|---|---|---|---|---|---|---|
| Serum | UBBC | | TC-I | | TC-II | | TC-III | |
| No. | mean ± s.d. | c.v. | mean ± s.d. | c.v. | mean ± s.d. | c.v. | mean ± s.d. | c.v. |
| 195 | 3289 ± 303 | 9.2 | 1630 ± 250 | 15.3 | 1140 ± 177 | 15.5 | 521 ± 125 | 24.0 |
| 276 | 4575 ± 323 | 7.1 | 1412 ± 118 | 8.3 | 882 ± 70 | 9.9 | 2280 ± 240 | 10.4 |

(c) Group 3: PV and leukocytosis cases

TABLE C

| | | Filter Stack Test Format | | | | |
|---|---|---|---|---|---|---|
| | | Polycythemia vera (PV) and leukocytosis | | | | |
| Patient Identi- No. fication | $B^{12}$ pg/ml | UBBC pg/ml | TCI pg/ml | TCII pg/ml | TCIII pg/ml | Remarks |
| 1 M.P | 400 | 1933 | 270 | 870 | 793 | |
| 2 M.S | 1250 | 3147 | 440 | 1320 | 1387 | |
| 3 V.H | 700 | 3352 | 370 | 969 | 2013 | |
| | 500 | 2941 | 299 | 964 | 1678 | following chemotherapy |
| 4 P.Y | 900 | 3352 | 335 | 1173 | 1844 | |
| 5 g.m | 870 | 2529 | 227 | 1466 | 836 | |
| 6 A.C | 400 | 2076 | 228 | 1079 | 769 | |
| 7 Y.Y | 650 | 2176 | 148 | 961 | 997 | |
| 8 S.M | 550 | 3384 | 378 | 1522 | 1486 | |
| 9 B.A | 750 | 6461 | 356 | 1609 | 4496 | |
| 10 M.P | 900 | 2424 | 387 | 1284 | 753 | |
| 11 B.A | 750 | 2852 | 370 | 1369 | 1113 | |
| 12 K.P | 400 | 2360 | 295 | 979 | 1086 | |
| | 950 | 1529 | 229 | 902 | 339 | following chemotherapy |
| 13 A.F | 700 | 2289 | 183 | 1533 | 572 | |
| 14 C.I | 200 | 1970 | 177 | 1319 | 474 | |
| 15 I.H | 370 | 2294 | 137 | 1468 | 689 | |
| 16 A.A | 700 | 2117 | 296 | 1587 | 234 | |
| 17 H.P | 800 | 2000 | 280 | 1040 | 680 | |
| 18 C.M | 1000 | 2424 | 387 | 1405 | 632 | |
| 19 C.Z | 810 | 1888 | 170 | 1379 | 339 | |
| 20 A.I | 400 | 2613 | 236 | 1672 | 705 | |
| 21 M.G | 900 | 1558 | 202 | 898 | 460 | |

In PV and leukocytosis there is elevation in UBBC due to increase in TCIII Binding capacity. No changes were noticed in $B_{12}$, TCI or TCII.

In active PV (PV in relapse) associated with increased leukocyte concentration there is an increase in TCIII serum concentration (patients Nos. 2,3,4,8,9, 11 and 12). In the non-active PV state with normal leukocyte concentration, TCIII is normal to slightly elevated (patients Nos. 1, 13–21). The TCIII binding capacity decreases during chemotherapy. (patients Nos. 3 and 12). Thus, the test for TCIII contributes to monitoring the course of active (relapse) PV stages, the response to chemotherapy treatments, and monitoring the non-active PV stages as well. More important, serum TCIII binding capacity determination helps in differentiation of leukemoid reactions and conditions manifested by nonleukemic leukocytosis.

(d) Group 4: Acute leukemia, Hodgkins disease and lymphoma cases

TABLE D

| | (Filter Stock Test Format) | | | | | |
|---|---|---|---|---|---|---|
| | Acute leukemia cases | | | | | |
| Patient Identi- No. fication | $B_{12}$ pg/ml | UBBC pg/ml | TCI pg/ml | TCII pg/ml | TCIII pg/ml | Remarks |
| 1 I.A | 1000 | 3647 | 291 | 2918 | 438 | |
| 2 P.M | 730 | 3763 | 452 | 2747 | 564 | |
| 3 P.N | 900 | 7568 | 203 | 6760 | 605 | |
| | 900 | 4018 | 201 | 3335 | 482 | Following chemotherapy |
| 4 K.H | 750 | 6000 | 400 | 5180 | 420 | |

TABLE D-continued
(Filter Stock Test Format)
Acute leukemia cases

| Patient No. | Identi-fication | $B_{12}$ pg/ml | UBBC pg/ml | TCI pg/ml | TCII pg/ml | TCIII pg/ml | Remarks |
|---|---|---|---|---|---|---|---|
| | | 750 | 3037 | 273 | 2581 | 183 | Following chemotherapy |
| | | 450 | 2545 | 127 | 2188 | 230 | Following chemotherapy |
| 5 | M.S | 270 | 2935 | 376 | 2431 | 410 | |
| | | 370 | 1900 | 171 | 1349 | 380 | Following chemotherapy |
| 6 | Z.H | 850 | 3364 | 471 | 2422 | 471 | |
| | | 700 | 236 | 306 | 1652 | 402 | Following chemotherapy |
| 7 | M.B | 900 | 3030 | 121 | 2545 | 364 | |
| | | 300 | 2000 | 140 | 1540 | 320 | Following chemotherapy |
| | | 450 | 1900 | 285 | 1240 | 375 | Following chemotherapy |
| | | 500 | 1360 | 136 | 984 | 240 | Following chemotherapy |
| 8 | B.A | 475 | 2650 | 291 | 1829 | 530 | |
| | | 600 | 2063 | 228 | 1583 | 247 | Following chemotherapy |
| 9 | H.M | 1000 | 2300 | 54 | 1771 | 276 | |
| | | 500 | 1700 | 173 | 986 | 571 | Following chemotherapy |
| 10 | Z.I | 580 | 2739 | 109 | 2492 | 137 | |
| | | 670 | 1834 | 129 | 1467 | 238 | Following chemotherapy |
| | | 700 | 2000 | 1258 | 1442 | 300 | Following chemotherapy |
| | | 900 | 1760 | 229 | 1355 | 176 | Following chemotherapy |
| 11 | H.H | 200 | 2360 | 277 | 1959 | 123 | |
| | | 870 | 1930 | 360 | 1258 | 674 | Following chemotherapy |
| 12 | N.A.A | 1200 | 2000 | 180 | 1460 | 360 | Protracted course |
| 13 | A.H.N | 650 | 2100 | 280 | 1400 | 420 | Protracted course |
| 14 | Z.I | 600 | 1760 | 119 | 1330 | 311 | Protracted course |
| 15 | G.M | 1070 | 1868 | 280 | 1309 | 280 | Protracted course |

(e) Group 5: Hodgkins disease and lymphoma cases

TABLE - E(1)
Filter Stack Format

| No | Patent Identi-fication | $B_{12}$ pg/ml | UBBC pg/ml | TCI pg/ml | TCII pg/ml | TCIII pg/ml | Remarks |
|---|---|---|---|---|---|---|---|
| 1 | B.S | 950 | 5300 | 380 | 4500 | 420 | |
| | | 500 | 1475 | 163 | 1012 | 300 | Following chemotherapy |
| 2 | Z.A | 720 | 4411 | 486 | 3514 | 411 | |
| 3 | I.P | 700 | 2615 | 235 | 2119 | 1261 | |
| 4 | A.A | 900 | 3600 | 180 | 3096 | 324 | |
| 5 | V.V | 500 | 4176 | 126 | 3490 | 551 | |
| 6 | V.A | 1000 | 5100 | 204 | 4384 | 512 | |
| 7 | L.H | 850 | 4650 | 372 | 3787 | 491 | |
| 8 | A.A | 450 | 3500 | 175 | 2905 | 420 | |
| 9 | K.I | 700 | 4900 | 434 | 3800 | 666 | |
| 10 | S.V | — | 4500 | 180 | 4005 | 315 | |
| 11 | I.X | — | 2910 | 175 | 2270 | 465 | |
| 12 | S.B | — | 1500 | 150 | 1020 | 330 | Protracted course |
| 13 | S.Z | — | 2100 | 147 | 1680 | 273 | Pretreated course |

Table D and E relating to acute leukemias, Hodgkins disease and lymphomas in which there is increase in UBBC due to elevation in TCII binding capacity. No changes were noticed in $B_{12}$, TCI or TCIII. The increase in TCII is in direct proportion to the acuteness of the disease. Increase in serum TCII binding capacity without a change in Vitamin $B_{12}$ level may indicate an acute proliferation of malignant cells of any kind (such as acute leukemia, Hodgkins disease, lymphomas, etc.). This finding may be useful in the recognition of rapid cell proliferation in malignant lymphoma and acute nondifferentiated leukemias. The TCII binding capacity decreases during chemotherapy and thus serves as a reliable criterion in the evaluation of the effect of the therapy. Patients during the protracted or remission course show normal ranges of TCII. However, during the proliferation of the malignant cells (the relapse stage) increase in TCII binding capacity is noticed. Thus, the test for TCII contributes to the monitoring of the relapse course of acute leukemias, Hodgkins disease, lymphomas, etc., the response to chemotherapy treatments and monitoring the protracted course or remission as well.

Using the double mini-column test format, a precision study was performed with clinical sera from pathological conditions. Representative results are given in Table E(2).

TABLE - E(2)

| Serum No. | Mini-Column Test Format | | | | | | | |
|---|---|---|---|---|---|---|---|---|
| | UBBC | | TC-I | | TC-II | | TC-III | |
| | mean ± s.d. | c.v. | mean ± s.d. | c.v. | mean ± s.d. | c.v. | mean ± s.d. | c.v. |
| 10 | 4910 ± 300 | 6.0 | 490 ± 85 | 17.3 | 3812 ± 215 | 5.6 | 640 ± 82 | 12.9 |

(f) Group 6: Hepatocellular damage

It is well established that increase in serum $B_{12}$ bound mainly to TCII is characteristic to hepatocellular damage. The $B_{12}$ released from the damaged liver cells saturates TCII and part of the TCI. As a result, serum binding capacity (UBBC) is very low while endogenous $B_{12}$ bound to TCII is increased. Since the filter-stack technique determines the UBBC of the binders, in hepatic diseases the TCII will be very low. This phenomena is already well recognized and accepted as a valuable diagnostic aid.

TEST KIT

The test kit comprises the essential elements required to perform the subject inventive process, namely, in a packaged combination, a container of a solution of $^{57}Co$ Vitamin B-12; a TC-II adsorbent, preferably as described above; a DEAE-cellulose adsorbent, preferably as described above; and a container of monopotassium phosphate solution of about 0.05 M and at a pH of about 4.6. Optionally, where the adsorbents are arranged in the filter stack configuration and the TC-II adsorbent is a cellulose nitrate filter, the kit additionally includes a container of borate solution of about 0.1 M and at a pH of about 8.5 as a wash for excess radioactive Vitamin B-12. On the other hand, where such adsorbents are arranged in the mini-column configuration and the TC-II adsorbent is granular silica gel, the kit optionally includes, as a wash liquid, phosphate buffer of about 0.02 M and at a pH of about 6.4. The activity of the radioactive Vitamin B-12 solution is preferably from 135–200 $\mu Ci/\mu g$.

SUMMARY

Determination of serum transcobalamins binding capacity is useful in diagnosis of the following diseases:

| Disease | Vitamin $B_{12}$ | UBBC of whole serum | Binding Capacity | | |
|---|---|---|---|---|---|
| | | | TCI | TCII | TCIII |
| CMA and APL | elevation | elevation | elevation | normal | elevation[1] |
| PV and leukocytosis | normal | elevation | normal | normal | elevation |
| AML, Hodgkins disease lymphoma | normal | elevation | normal | elevation | normal |
| Hepatocellular damage | elevation | decrease | normal | decrease | normal |

[1] in chronic cases

Serum transcobalamins binding capacity determination is also useful in monitoring the relapse courses of these diseases, the response to chemotherapy treatments and monitoring the protracted or remission courses as well.

In summary, the three transcobalamins undergo specific quantitative changes during certain clinical pathological conditions. The research done on this subject during the last few years has proved beyond any doubt the clinical significance of the changes in the transcobalamins binding capacity. The determination of the various serum transcobalamins binding capacity is today an important tool in diagnosis as well as in evaluation of the effects of treatment.

What is claimed is:

1. A method for the quantitative determination of the individual and total unsaturated Vitamin B-12 binding capacities of the three transcobalamins TC-I, TC-II, and TC-III in serum, which method comprises the steps of incubating a predetermined quantity of serum with a solution of $^{57}Co$ Vitamin B-12 whereby the unsaturated Vitamin B-12 binding sites on the transcobalamins in said quantity of serum become occupied by the radioactive Vitamin B-12; contacting the resulting mixture with (a) a TC-II adsorbent whereby the TC-II from said quantity of serum becomes adsorbed thereto, and (b) a DEAE-cellulose adsorbent whereby the TC-I and TC-III from said quantity of serum becomes adsorbed thereto; washing away from said adsorbents the $^{57}Co$ Vitamin B-12 not bound to any of the transcobalamins; measuring the total radioactivity of said adsorbents, which radioactivity is a function of the total unsaturated Vitamin B-12 binding capacity of the serum tested; selectively desorbing TC-III from said DEAE-cellulose by washing with a monopotassium phosphate solution of about 0.05 M and at a pH of about 4.6; measuring the individual radioactivity of said adsorbents, which radioactivity of said TC-II adsorbent is a function of the TC-II unsaturated Vitamin B-12 binding capacity of the serum tested and that of said DEAE-cellulose adsorbent is a function of the TC-I unsaturated Vitamin B-12 binding capacity of the serum tested; and calculating the difference in radioactivity of said total radioactivity measurement and the sum of said individual radioactivity measurements, which difference is a function of the TC-III unsaturated Vitamin B-12 binding capacity of the serum tested.

2. The method of claim 1 wherein the radioactivity values corresponding to the total TC-I, TC-II, and TC-III unsaturated Vitamin B-12 binding capacities of the serum tested are converted to Vitamin B-12 concentration values by comparison of said total radioactivity measurement to the radioactivity of a solution of $^{57}Co$ Vitamin B-12 of known concentration and calculating the fractions thereof attributable to TC-I, TC-II, and TC-III.

3. The method of claim 1 wherein said TC-II adsorbent is made of a charged cellulose material.

4. The method of claim 3 wherein said TC-II adsorbent is a cellulose nitrate filter.

5. The method of claim 1 wherein said TC-II adsorbent is made of a silica material.

6. The method of claim 5 wherein said TC-II adsorbent is granular silica gel.

7. The method of claim 1 wherein said DEAE-cellulose adsorbent is in the form of a filter.

8. The method of claim 1 wherein said DEAE-cellulose adsorbent is in a granular form.

9. The method of claim 1 wherein said adsorbents are arranged as a stack of a cellulose nitrate filter and a DEAE-cellulose filter.

10. The method of claim 1 wherein said adsorbents are arranged as a stackable pair of columns, one containing granular silica gel and the other granular DEAE-cellulose.

11. A test kit for the quantitative determination of the individual and total unsaturated Vitamin B-12 binding capacity of the three transcobalamins TC-I, TC-II, and TC-III in serum, comprising, in a packaged combination, a container of a solution of $^{57}$Co Vitamin B-12; a TC-II adsorbent; a DEAE-cellulose adsorbent; and a container of monopotassium phosphate solution of about 0.05 M and at a pH of about 4.6.

12. The test kit of claim 11 wherein said TC-II adsorbent is made of a charged cellulose material.

13. The test kit of claim 12 wherein said TC-II adsorbent is a cellulose nitrate filter.

14. The test kit of claim 11 wherein said TC-II adsorbent is made of a silica material.

15. The test kit of claim 14 wherein said TC-II adsorbent is granular silica gel.

16. The test kit of claim 11 wherein said DEAE-cellulose adsorbent is in the form of a filter.

17. The test kit of claim 11 wherein said DEAE-cellulose adsorbent is in a granular form.

18. The test kit of claim 11 wherein said adsorbents are arranged as a stack of a cellulose nitrate filter and a DEAE-cellulose filter.

19. The test kit of claim 18 which additionally comprises a container of borate solution of about 0.1 M and at a pH of about 8.5.

20. The test kit of claim 11 wherein said adsorbents are arranged as a stackable pair of columns, one containing granular silica gel and the other granular DEAE-cellulose.

21. The test kit of claim 20 which additionally comprises a container of phosphate solution of about 0.02 M and at a pH of about 6.4.

22. The test kit of claim 11 wherein the $^{57}$Co Vitamin B-12 is of an activity of from 135–200 $\mu$Ci/$\mu$g.

* * * * *